US 8,961,564 B2

(12) United States Patent
Gordon et al.

(10) Patent No.: US 8,961,564 B2
(45) Date of Patent: Feb. 24, 2015

(54) BONE TISSUE CLAMP

(71) Applicants: Charles Gordon, Tyler, TX (US); Marc C. Yap, Carlsbad, CA (US)

(72) Inventors: Charles Gordon, Tyler, TX (US); Marc C. Yap, Carlsbad, CA (US)

(73) Assignee: OsteoMed LLC, Addison, TX (US)

( * ) Notice: Subject to any disclaimer, the term of this patent is extended or adjusted under 35 U.S.C. 154(b) by 0 days.

(21) Appl. No.: 13/709,251

(22) Filed: Dec. 10, 2012

(65) Prior Publication Data

US 2013/0103089 A1 Apr. 25, 2013

Related U.S. Application Data

(63) Continuation of application No. 12/820,575, filed on Jun. 22, 2010, now Pat. No. 8,377,097.

(60) Provisional application No. 61/219,687, filed on Jun. 23, 2009.

(51) Int. Cl.
*A61B 17/70* (2006.01)
(52) U.S. Cl.
CPC ......... *A61B 17/7047* (2013.01); *A61B 17/7062* (2013.01)
USPC .......................................... 606/248; 606/249
(58) Field of Classification Search
CPC ........... A61B 17/7047; A61B 17/7056; A61B 17/7062; A61B 17/7068
USPC ................................. 606/90, 246, 248, 249; 623/17.11–17.16
See application file for complete search history.

(56) References Cited

U.S. PATENT DOCUMENTS

| 3,242,922 | A | 3/1966 | Thomas |
| 3,469,573 | A | 9/1969 | Florio |
| 3,648,691 | A | 3/1972 | Lumb et al. |
| 4,066,082 | A | 1/1978 | Arcan et al. |
| 4,290,328 | A | 9/1981 | Clark |
| D281,814 | S | 12/1985 | Pratt et al. |
| 4,570,623 | A | 2/1986 | Ellison et al. |
| 4,592,346 | A | 6/1986 | Jurgutis |
| 4,848,328 | A | 7/1989 | Laboureau et al. |

(Continued)

FOREIGN PATENT DOCUMENTS

| EP | 1477124 B1 | 10/2007 |
| JP | 2004-535239 A | 11/2004 |

(Continued)

OTHER PUBLICATIONS

Bostman et al., "Posterior Spinal Fusion Using Internal Fixation with the Daab Plate," Acta. Orthop. Scand., vol. 55, pp. 310-314, 1984.
International Search Report and Written Opinion issued in International Application No. PCT/US08/88204, mailed Feb. 12, 2009.

(Continued)

*Primary Examiner* — Mary Hoffman
*Assistant Examiner* — Christina Negrellirodriguez
(74) *Attorney, Agent, or Firm* — Fulbright & Jaworski LLP

(57) ABSTRACT

Systems, methods, and kits incorporate a fusion member for vertebral processes. The fusion member may be unitary or modular. The fusion member comprises extensions configured to be crimped to vertebral processes. The extensions may comprise tabs configured to be deformed to further penetrate the vertebral processes. The tabs may also lock together modular components of the fusion member. The fusion member may comprise fasteners extending between the extensions. The fusion member may comprise a cage with a movable cover or a graft retention feature.

26 Claims, 17 Drawing Sheets

(56) References Cited

U.S. PATENT DOCUMENTS

| | | | |
|---|---|---|---|
| 4,852,558 A | 8/1989 | Outerbridge | |
| 4,913,144 A | 4/1990 | Del Medico | |
| 4,994,073 A | 2/1991 | Green | |
| 5,007,909 A | 4/1991 | Rogozinski | |
| 5,011,484 A | 4/1991 | Beard | |
| 5,053,038 A | 10/1991 | Sheehan | |
| 5,074,864 A | 12/1991 | Cozad et al. | |
| 5,108,422 A | 4/1992 | Green et al. | |
| 5,196,318 A | 3/1993 | Baldwin et al. | |
| 5,201,746 A | 4/1993 | Shichman | |
| 5,246,442 A | 9/1993 | Ashman et al. | |
| 5,261,909 A | 11/1993 | Sutterlin et al. | |
| 5,290,312 A | 3/1994 | Kojimoto et al. | |
| 5,395,370 A | 3/1995 | Muller et al. | |
| 5,454,814 A | 10/1995 | Comte | |
| 5,496,318 A | 3/1996 | Howland et al. | |
| 5,609,634 A | 3/1997 | Voydeville | |
| 5,611,800 A | 3/1997 | Davis et al. | |
| 5,626,592 A | 5/1997 | Phillips et al. | |
| 5,645,599 A | 7/1997 | Samani | |
| 5,713,911 A | 2/1998 | Racenet et al. | |
| 5,722,976 A | 3/1998 | Brown | |
| 5,836,948 A | 11/1998 | Zucherman et al. | |
| 5,853,414 A | 12/1998 | Groiso | |
| 5,893,889 A | 4/1999 | Harrington | |
| 5,941,881 A | 8/1999 | Barnes | |
| 6,007,538 A | 12/1999 | Levin | |
| 6,148,696 A | 11/2000 | Chiang | |
| 6,238,397 B1 | 5/2001 | Zucherman et al. | |
| 6,312,431 B1 | 11/2001 | Asfora | |
| 6,332,883 B1 | 12/2001 | Zucherman et al. | |
| 6,336,928 B1 | 1/2002 | Guerin et al. | |
| 6,352,537 B1 | 3/2002 | Strnad | |
| 6,364,883 B1 | 4/2002 | Santilli | |
| 6,375,683 B1 | 4/2002 | Crozet et al. | |
| 6,379,355 B1 | 4/2002 | Zucherman et al. | |
| 6,440,169 B1 * | 8/2002 | Elberg et al. | 623/17.16 |
| 6,443,987 B1 | 9/2002 | Bryan | |
| 6,451,019 B1 | 9/2002 | Zucherman et al. | |
| 6,485,518 B1 | 11/2002 | Cornwall et al. | |
| 6,558,387 B2 | 5/2003 | Errico et al. | |
| 6,565,573 B1 | 5/2003 | Ferrante et al. | |
| 6,582,435 B2 | 6/2003 | Wellisz et al. | |
| 6,641,585 B2 | 11/2003 | Sato et al. | |
| 6,695,842 B2 | 2/2004 | Zucherman et al. | |
| 6,699,247 B2 | 3/2004 | Zucherman et al. | |
| 6,712,819 B2 | 3/2004 | Zucherman et al. | |
| 6,761,720 B1 | 7/2004 | Senegas | |
| 6,783,531 B2 | 8/2004 | Allen | |
| 6,796,983 B1 | 9/2004 | Zucherman et al. | |
| 6,923,812 B1 | 8/2005 | Wellisz | |
| 6,969,391 B1 | 11/2005 | Gazzani | |
| 7,025,787 B2 | 4/2006 | Bryan et al. | |
| 7,048,736 B2 | 5/2006 | Robinson et al. | |
| 7,060,068 B2 | 6/2006 | Tromanhauser et al. | |
| 7,229,444 B2 | 6/2007 | Boyd | |
| 7,250,060 B2 | 7/2007 | Trieu | |
| 7,255,698 B2 | 8/2007 | Michelson | |
| 7,294,128 B2 | 11/2007 | Alleyne et al. | |
| 7,335,203 B2 | 2/2008 | Winslow et al. | |
| 7,377,921 B2 | 5/2008 | Studer et al. | |
| 7,393,361 B2 | 7/2008 | Zubok et al. | |
| 7,396,360 B2 | 7/2008 | Lieberman | |
| 7,588,592 B2 | 9/2009 | Winslow et al. | |
| 7,666,228 B2 | 2/2010 | Le Couedic et al. | |
| 7,727,233 B2 | 6/2010 | Blackwell et al. | |
| 7,857,857 B2 * | 12/2010 | Kim | 623/17.16 |
| 7,862,592 B2 | 1/2011 | Peterson et al. | |
| 7,871,426 B2 | 1/2011 | Chin et al. | |
| 7,935,133 B2 | 5/2011 | Malek | |
| 7,955,392 B2 | 6/2011 | Dewey et al. | |
| 8,043,337 B2 | 10/2011 | Klyce et al. | |
| 8,048,120 B1 | 11/2011 | Fallin et al. | |
| 8,070,817 B2 | 12/2011 | Gradl et al. | |
| 8,114,132 B2 | 2/2012 | Lyons et al. | |
| 8,128,659 B2 | 3/2012 | Ginsberg et al. | |
| 8,157,842 B2 | 4/2012 | Phan et al. | |
| 2001/0020188 A1 | 9/2001 | Sander | |
| 2003/0040746 A1 | 2/2003 | Mitchell et al. | |
| 2003/0045877 A1 | 3/2003 | Yeh | |
| 2003/0216736 A1 | 11/2003 | Robinson et al. | |
| 2004/0034430 A1 | 2/2004 | Falahee | |
| 2004/0106995 A1 * | 6/2004 | Le Couedic et al. | 623/17.11 |
| 2004/0193272 A1 | 9/2004 | Zubok et al. | |
| 2005/0043732 A1 | 2/2005 | Dalton | |
| 2005/0056979 A1 | 3/2005 | Studer et al. | |
| 2005/0137594 A1 | 6/2005 | Doubler et al. | |
| 2005/0216017 A1 | 9/2005 | Fielding et al. | |
| 2005/0234459 A1 | 10/2005 | Falahee et al. | |
| 2005/0256582 A1 | 11/2005 | Ferree | |
| 2006/0004367 A1 | 1/2006 | Alamin et al. | |
| 2006/0074425 A1 | 4/2006 | Sutterlin et al. | |
| 2006/0142771 A1 | 6/2006 | Beutter | |
| 2006/0235391 A1 | 10/2006 | Sutterlin | |
| 2006/0235518 A1 | 10/2006 | Blain | |
| 2006/0241601 A1 | 10/2006 | Trautwein et al. | |
| 2006/0247623 A1 | 11/2006 | Anderson et al. | |
| 2006/0247634 A1 | 11/2006 | Warner et al. | |
| 2006/0247640 A1 | 11/2006 | Blackwell et al. | |
| 2006/0287654 A1 | 12/2006 | Posnick | |
| 2007/0016189 A1 | 1/2007 | Lake et al. | |
| 2007/0093823 A1 | 4/2007 | Booth et al. | |
| 2007/0162001 A1 | 7/2007 | Chin et al. | |
| 2007/0179500 A1 | 8/2007 | Chin et al. | |
| 2007/0191844 A1 | 8/2007 | Carls et al. | |
| 2007/0233082 A1 | 10/2007 | Chin et al. | |
| 2007/0250065 A1 | 10/2007 | Efron et al. | |
| 2007/0270812 A1 | 11/2007 | Peckham | |
| 2007/0270840 A1 | 11/2007 | Chin et al. | |
| 2007/0276384 A1 | 11/2007 | Spratt | |
| 2007/0276500 A1 | 11/2007 | Zucherman et al. | |
| 2008/0021471 A1 | 1/2008 | Winslow et al. | |
| 2008/0021472 A1 | 1/2008 | Winslow et al. | |
| 2008/0103512 A1 | 5/2008 | Gately | |
| 2008/0140125 A1 | 6/2008 | Mitchell et al. | |
| 2008/0147190 A1 | 6/2008 | Dewey et al. | |
| 2008/0177330 A1 | 7/2008 | Ralph et al. | |
| 2008/0183211 A1 * | 7/2008 | Lamborne et al. | 606/249 |
| 2008/0183218 A1 | 7/2008 | Mueller et al. | |
| 2008/0228225 A1 * | 9/2008 | Trautwein et al. | 606/246 |
| 2008/0243185 A1 | 10/2008 | Felix et al. | |
| 2008/0243186 A1 | 10/2008 | Abdou | |
| 2008/0281359 A1 | 11/2008 | Abdou | |
| 2009/0018658 A1 | 1/2009 | Garcia | |
| 2009/0062918 A1 | 3/2009 | Wang et al. | |
| 2009/0216272 A1 | 8/2009 | Currier et al. | |
| 2009/0216273 A1 | 8/2009 | Cox | |
| 2009/0264927 A1 | 10/2009 | Ginsberg et al. | |
| 2009/0270918 A1 | 10/2009 | Attia et al. | |
| 2009/0326589 A1 | 12/2009 | Lemoine et al. | |
| 2010/0036419 A1 | 2/2010 | Patel et al. | |
| 2010/0087860 A1 | 4/2010 | Chin et al. | |
| 2010/0241167 A1 | 9/2010 | Taber et al. | |
| 2010/0318127 A1 | 12/2010 | Phan et al. | |
| 2011/0029020 A1 | 2/2011 | Gordon et al. | |
| 2011/0054531 A1 | 3/2011 | Lamborne et al. | |
| 2011/0066186 A1 | 3/2011 | Boyer, II et al. | |
| 2011/0144692 A1 | 6/2011 | Saladin et al. | |
| 2011/0166600 A1 | 7/2011 | Lamborne et al. | |
| 2011/0224731 A1 | 9/2011 | Smisson, III et al. | |
| 2011/0224740 A1 | 9/2011 | Smisson, III et al. | |
| 2011/0313458 A1 | 12/2011 | Butler et al. | |
| 2011/0319936 A1 | 12/2011 | Gordon et al. | |
| 2012/0010662 A1 | 1/2012 | O'Neil et al. | |
| 2012/0016418 A1 | 1/2012 | Chin et al. | |
| 2012/0078304 A1 | 3/2012 | Jensen et al. | |
| 2012/0078305 A1 | 3/2012 | Wang et al. | |
| 2012/0083844 A1 | 4/2012 | Linares | |
| 2012/0083846 A1 | 4/2012 | Wallenstein et al. | |

(56) References Cited

U.S. PATENT DOCUMENTS

| | | |
|---|---|---|
| 2012/0089184 A1 | 4/2012 | Yeh |
| 2012/0095512 A1 | 4/2012 | Nihalani |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109205 A1 | 5/2012 | Mitchell et al. |
| 2012/0123475 A1 | 5/2012 | Ahn et al. |
| 2012/0136390 A1 | 5/2012 | Butler et al. |
| 2012/0143252 A1 | 6/2012 | Robinson |
| 2012/0150228 A1 | 6/2012 | Zappacosta et al. |
| 2012/0158061 A1 | 6/2012 | Koch et al. |
| 2012/0158063 A1 | 6/2012 | Altarac et al. |
| 2012/0310292 A1 | 12/2012 | Smisson, III et al. |

FOREIGN PATENT DOCUMENTS

| | | |
|---|---|---|
| WO | WO-00/62693 A1 | 10/2000 |
| WO | WO-2007/070819 A2 | 6/2007 |
| WO | WO-2007/109402 A2 | 9/2007 |
| WO | WO-2009/086397 A2 | 7/2009 |
| WO | WO-03/007829 A1 | 1/2013 |

OTHER PUBLICATIONS

International Search Report and Written Opinion issued in international Application No. PCT/US2008/088196, mailed Apr. 23, 2009.
Lanx, "Aspen Spinous Process System Product Brochure," www.lanx.com, Dec. 16, 2008.
Lanx, "Aspen Spinous Process System," http://www.spineansi.com/080607_Aspen_Lab_Presentation.ppt, last accessed Jun. 10, 1999.
Oregon Health & Science University, "OHSU Surgeons Find New Way to Fix Painful Broken Ribs," http://www.ohsu.edu/ohsuedu/newspub/releases/062706ribs.cfm, Jun. 27, 2006.
Saint John's Health Center, "Saint John's Spine Surgeion Uses ILIF Procedure to Treat Lumbar Spinal Stenosis," www.medicalnewstoday.com/articles/155013.php.
Sénégas, "Minimally Invasive Dynamic Stabilisation of the Lumbar Motion Segment with an Interspinous Implant," Minimally Invasive Spine Surgery, pp. 459-465, 2006.
U.S. Appl. No. 60/724,632 entitled "Inter-spinous Orthopedic Device Placement and Method of Use," filed Oct. 7, 2005.
"Globus Medical; SP-Fix Spinous Process Fixation Plate: Surgical Technique, pp. 1-32 Jan. 2011".

* cited by examiner

BONE TISSUE CLAMP

CROSS-REFERENCE TO RELATED APPLICATIONS

This application is a continuation of:

U.S. application Ser. No. 12/820,575, filed Jun. 22, 2010, entitled BONE TISSUE CLAMP.

U.S. application Ser. No. 12/820,575 claims the benefit of U.S. Application No. 61/219,687, filed Jun. 23, 2009, entitled BONE TISSUE CLAMP.

The above-referenced documents are hereby incorporated by reference in their entirety.

This application incorporates by reference each of the following applications in its entirety:

U.S. Provisional Patent Application 61/017,336, filed Dec. 28, 2007, entitled BONE TISSUE CLAMP;

U.S. Provisional Patent Application 61/023,327, filed Jan. 24, 2008, entitled BONE TISSUE CLAMP;

U.S. Provisional Patent Application 61/104,199, filed Oct. 9, 2008, entitled BONE TISSUE CLAMP;

U.S. Provisional Patent Application 61/108,368, filed Oct. 24, 2008, entitled BONE TISSUE CLAMP;

International Patent Application No. PCT/US2008/088196, filed Dec. 23, 2008, entitled BONE TISSUE FIXATION DEVICE AND METHOD; and U.S. patent application Ser. No. 12/342,816, filed Dec. 23, 2008, entitled BONE TISSUE FIXATION DEVICE AND METHOD.

BACKGROUND OF THE INVENTION

1. The Field of the Invention

Exemplary embodiments of the present disclosure comprise a device that can be secured to bone tissue and methods of securing the devices. In specific exemplary embodiments, a device may be secured to spinous processes of vertebral bodies. In other exemplary embodiments, a device may be secured to a calvarial flap or other bone tissue.

2. Description of Related Art

The pedicle screw is a common medical device currently used to attach components to a patient's vertebrae. While providing a stable platform to attach components to vertebrae, the pedicle screw has inherent drawbacks in its use. Such drawbacks include the difficulty in accessing the portion of the vertebrae needed to insert the pedicle screw. In addition, there are risks of serious injuries to the patient when using a pedicle screw to penetrate a vertebra in a region close to the nerves of the spinal cord.

Systems and methods for treatment for various spinal conditions have been disclosed in U.S. Pat. Nos. 5,645,599 and 6,440,169, incorporated herein by reference. Additional systems and methods of treatment have been disclosed in "Interspinous Process Decompression for Neurogenic Intermittent Claudication Secondary to Degenerative Lumbar Spinal Stenosis", Global Surgery—Future Directions 2005 by Patrick Simons, also incorporated herein by reference.

SUMMARY OF THE INVENTION

Exemplary embodiments of the present disclosure provide novel systems, kits, and methods for securing medical devices to bones for use in treatment of spinal conditions and other medical conditions where securement to bone tissue is needed.

BRIEF DESCRIPTION OF THE DRAWINGS

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, different materials of construction may be used for the insert employed in the kit or system. Furthermore, the shape of insert may also be altered.

Figure 1:
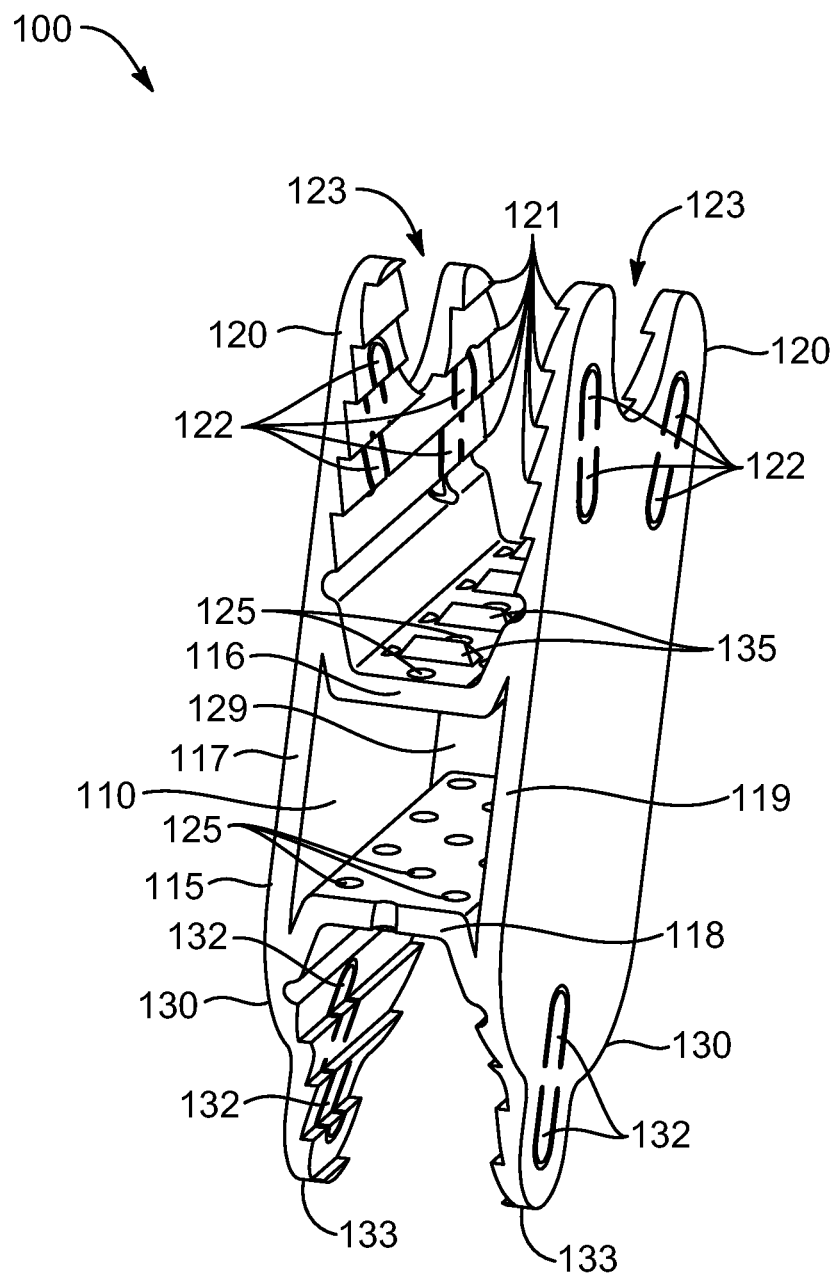

In the following Detailed Description, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear. Similar reference numbers (e.g., those that are identical except for the first numeral) are used to indicate similar features in different embodiments.

Figure 2:
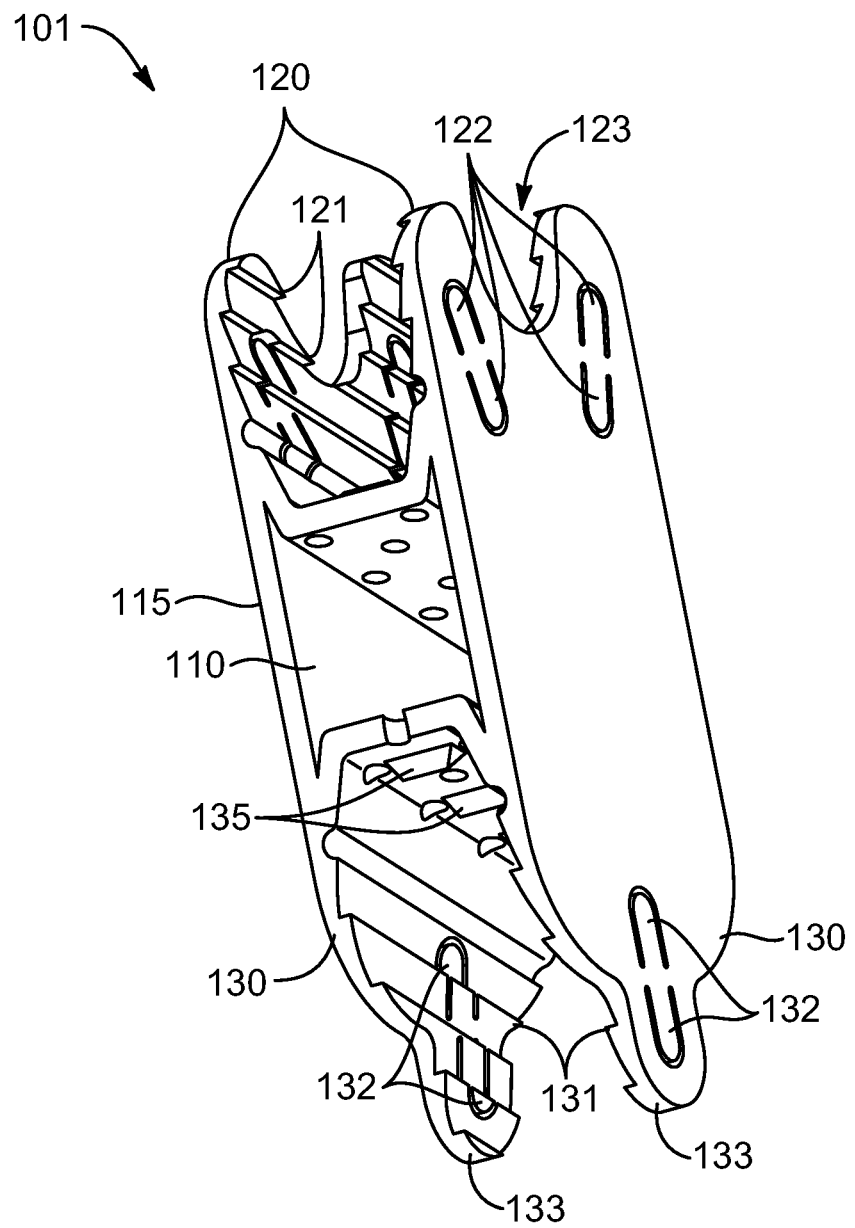
Figure 3:
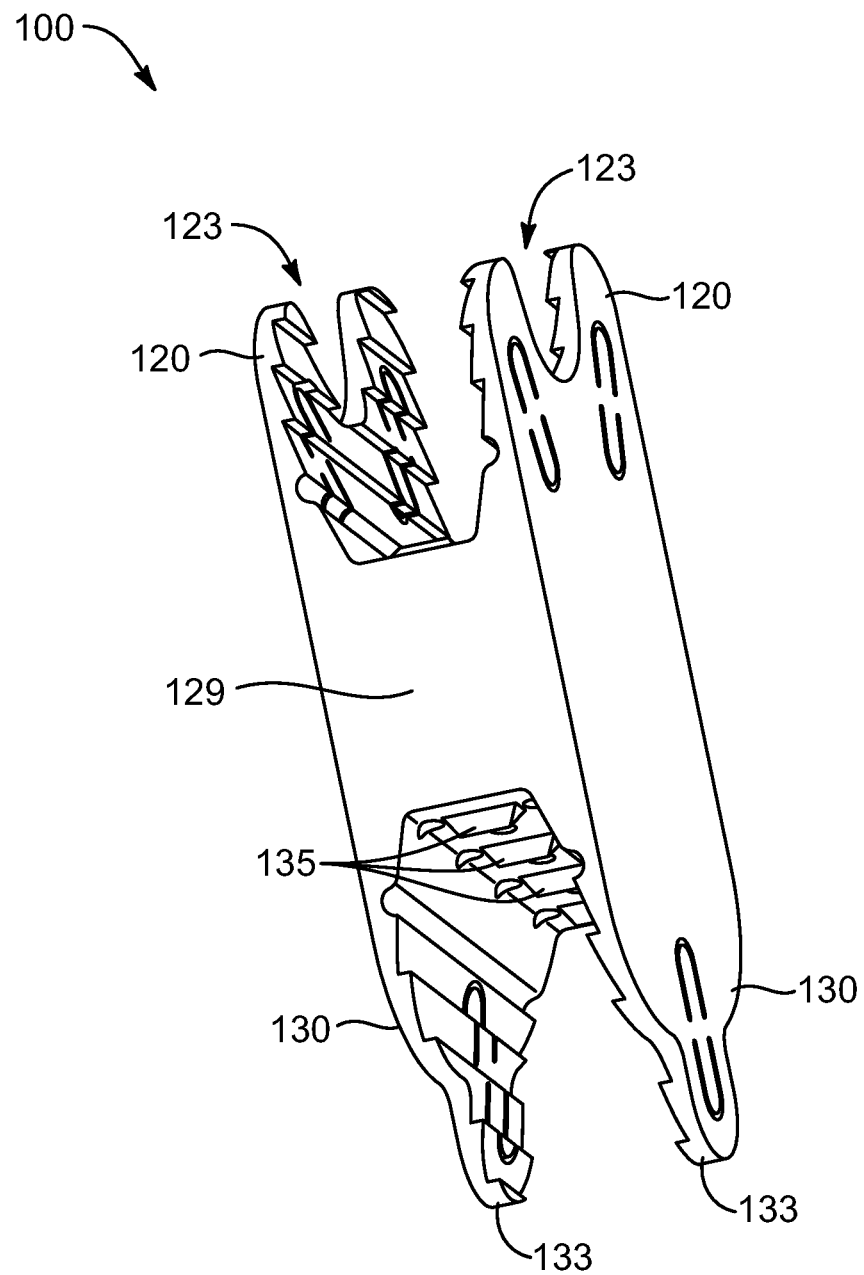
Figure 4:
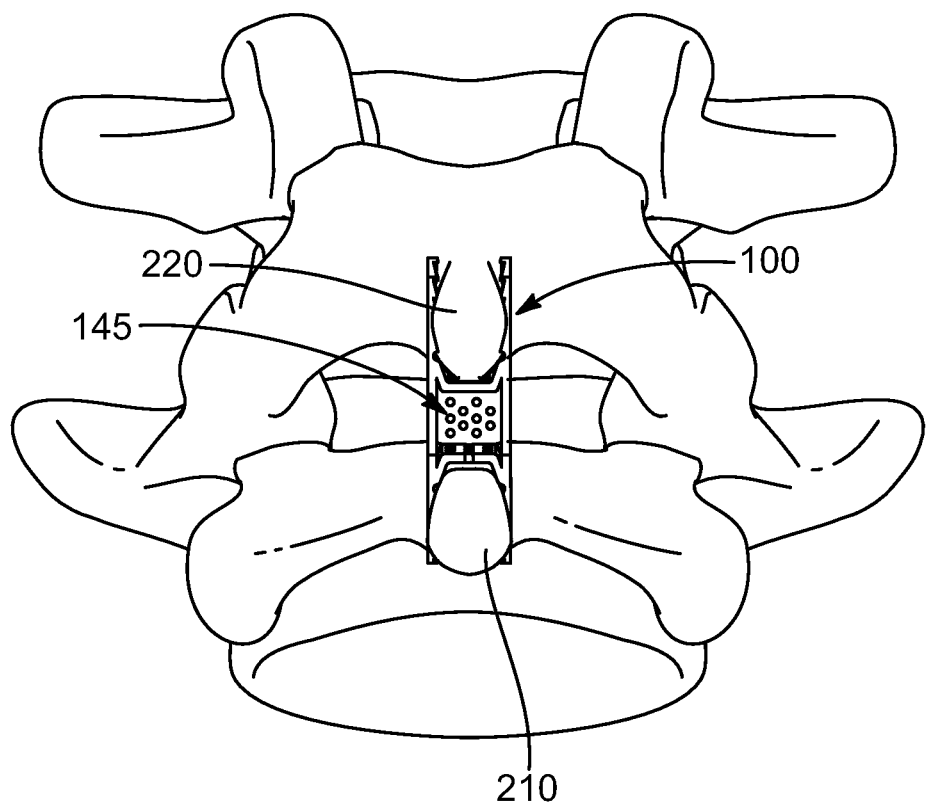
Figure 5:
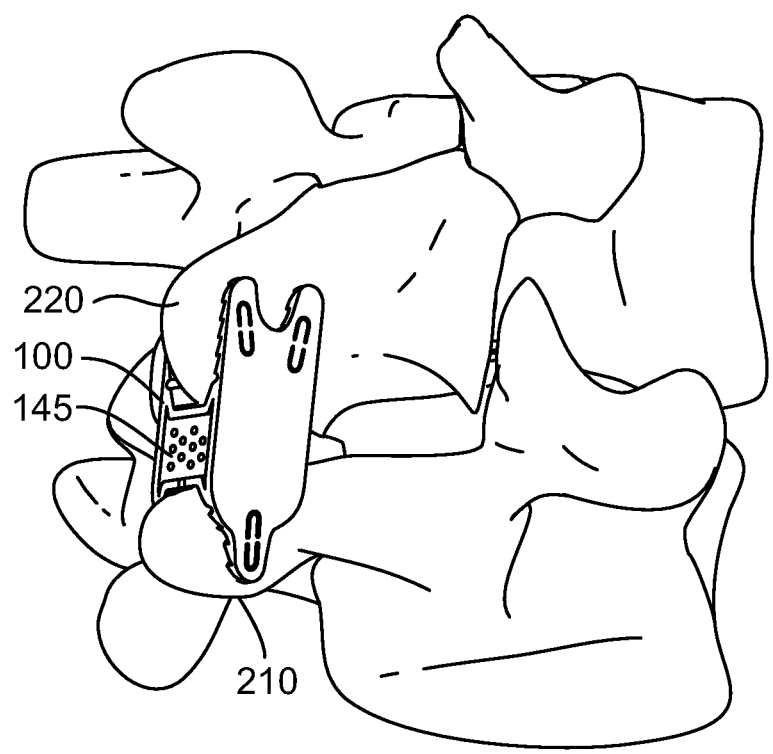
Figure 6:
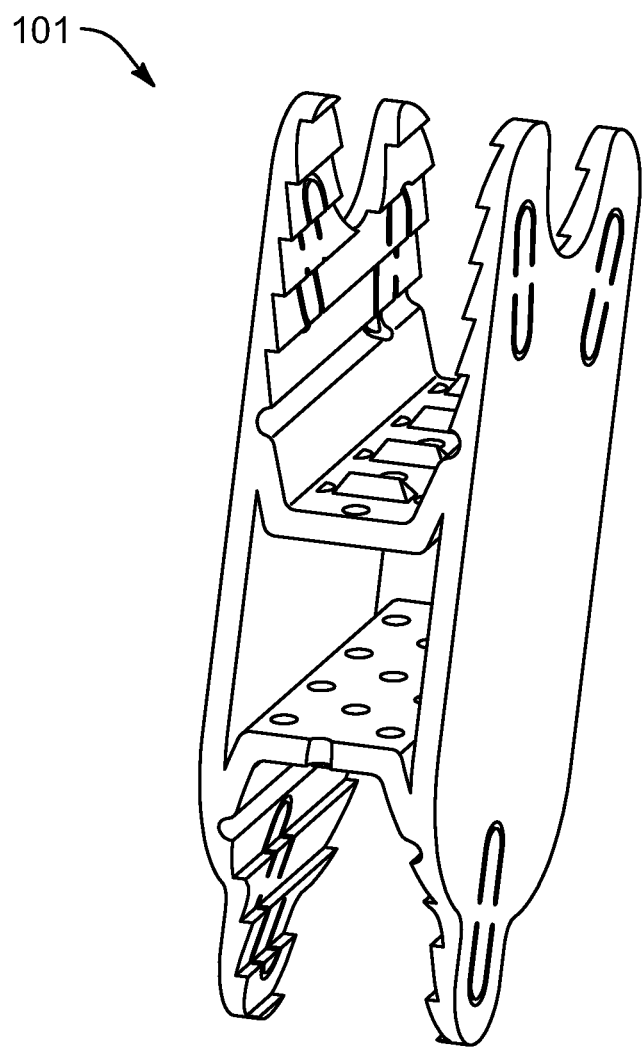
Figure 7:
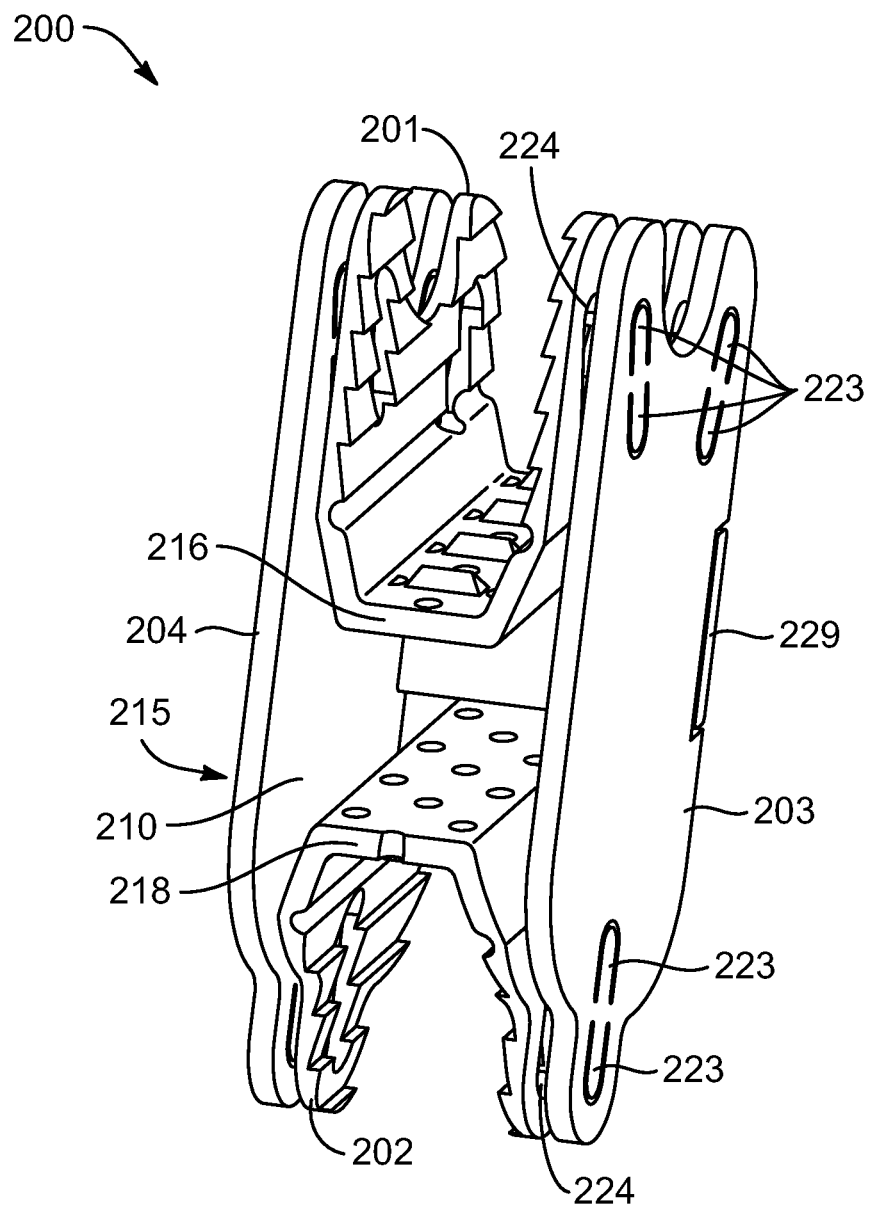
Figure 8:
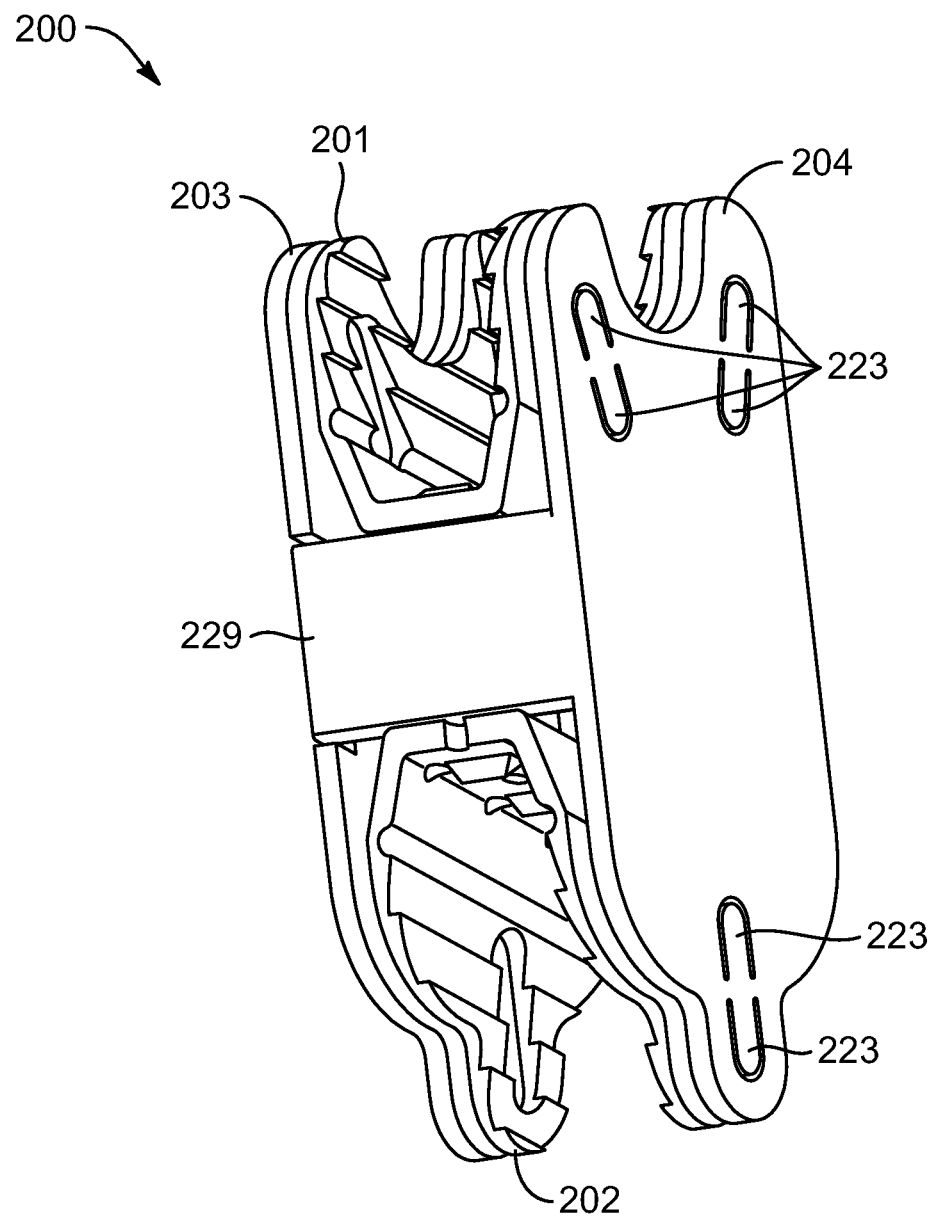
Figure 9:
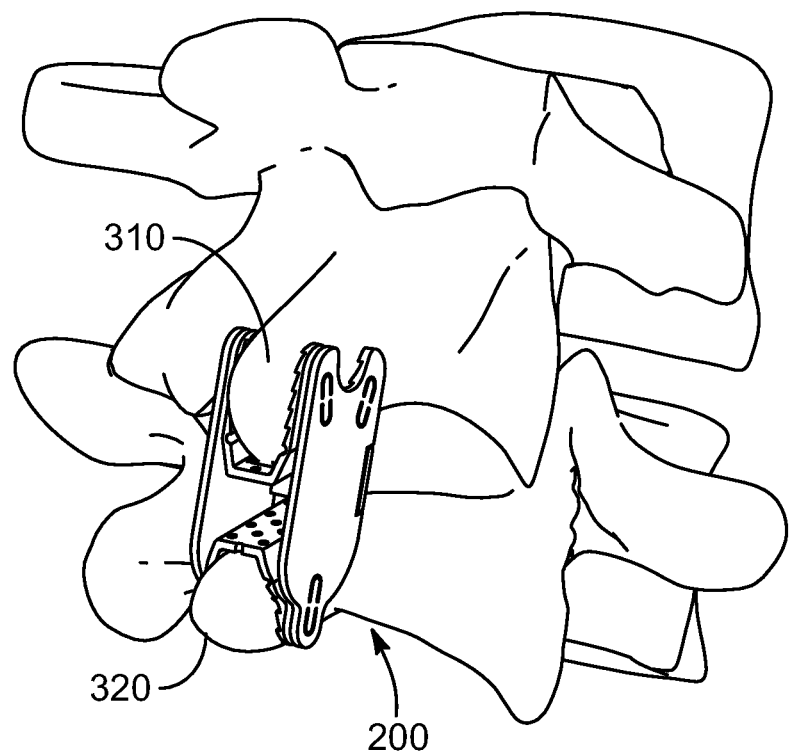
Figure 10:
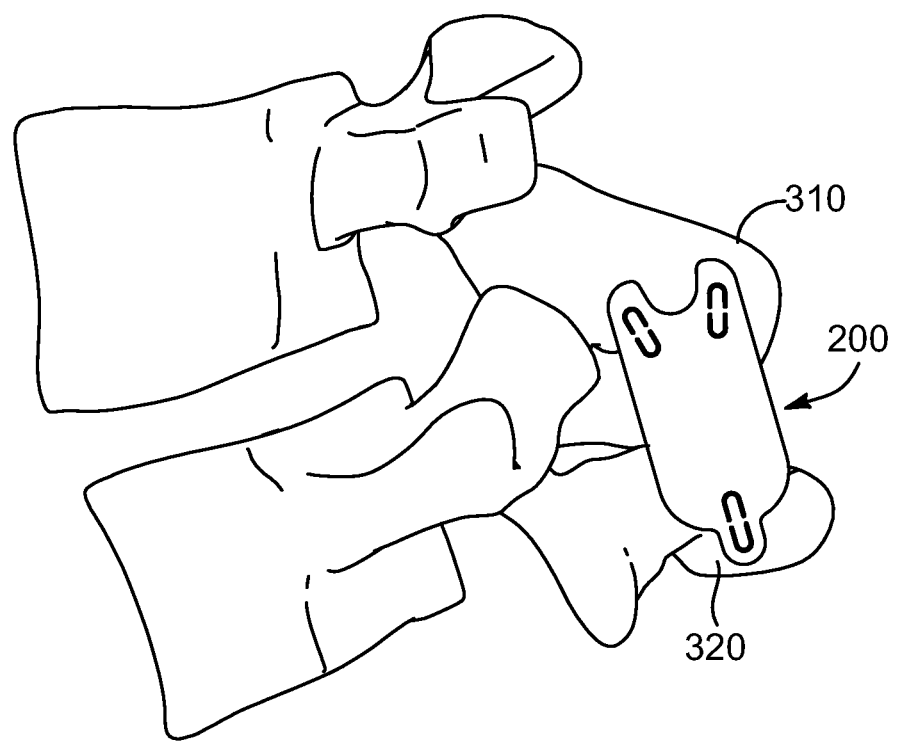
Figure 11:
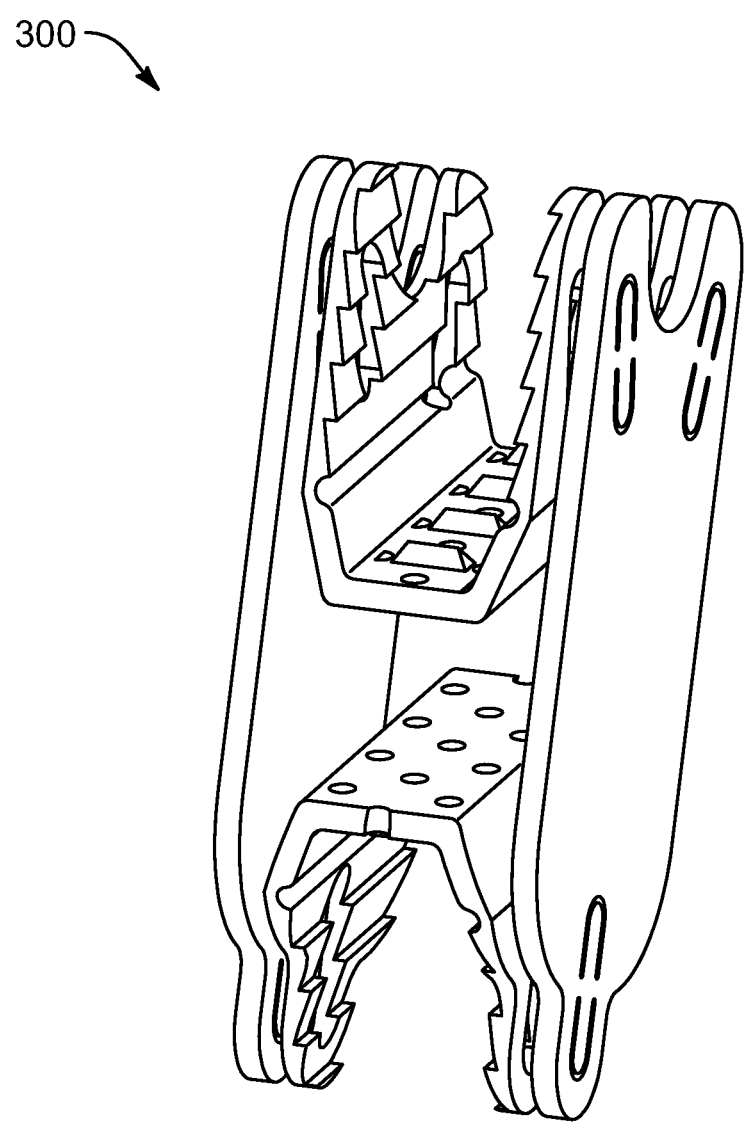
Figure 12:
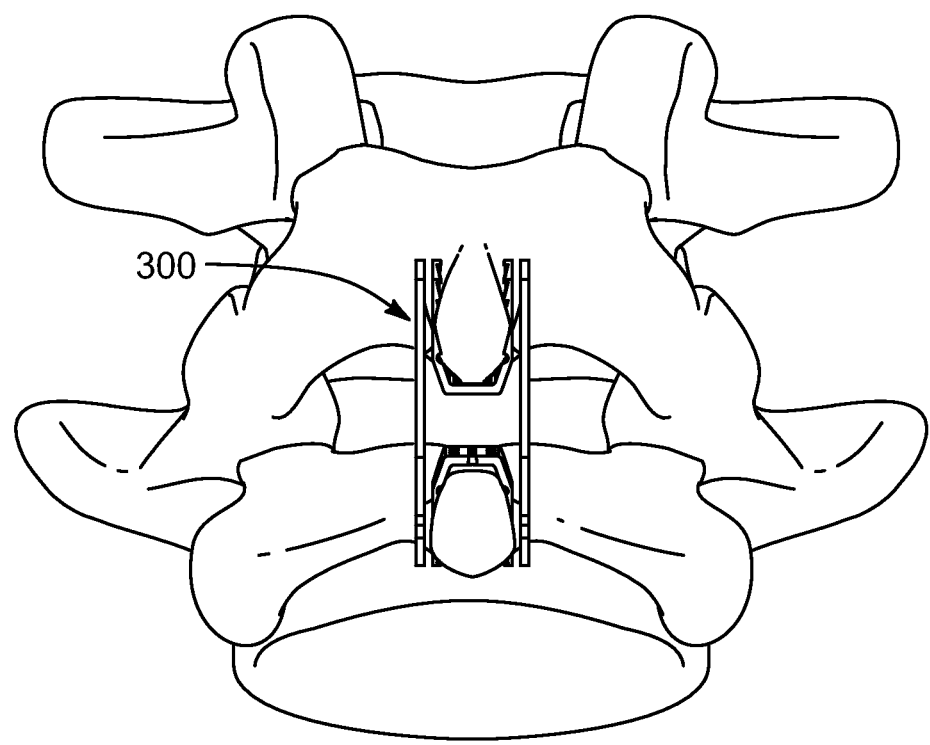
Figure 13:
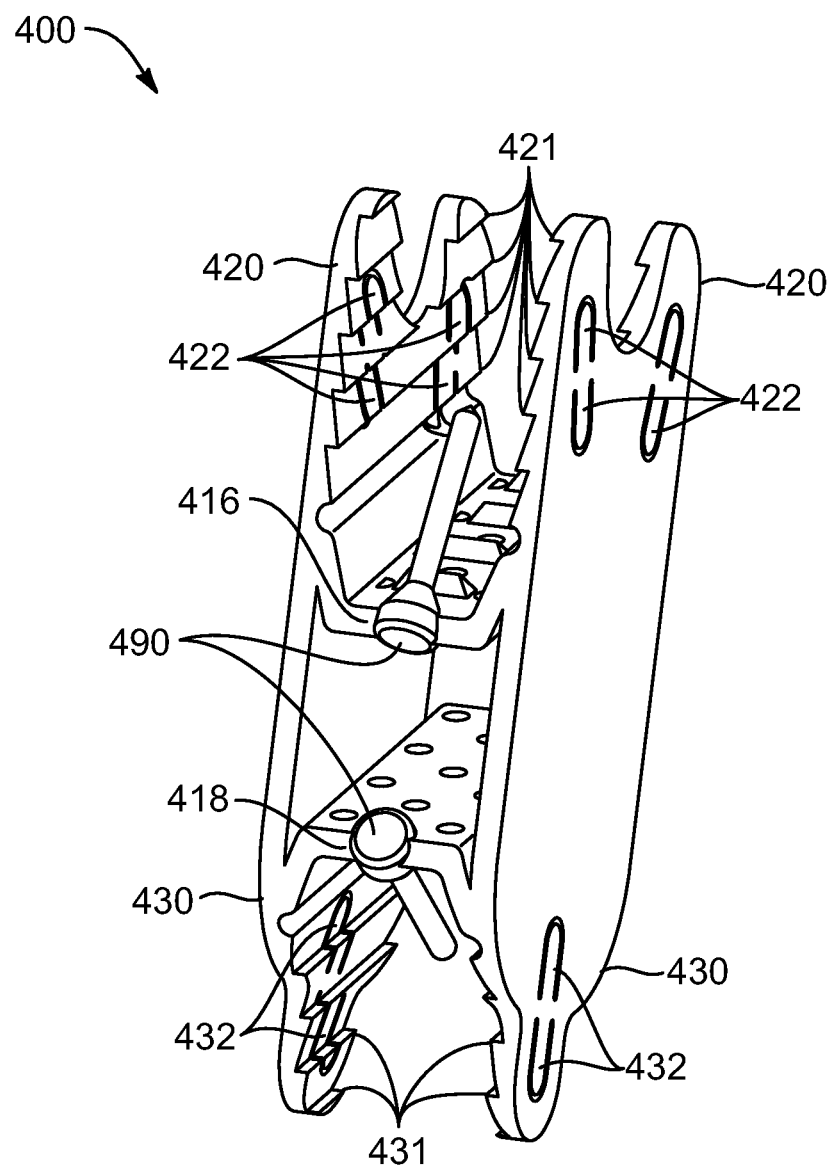
Figure 14:
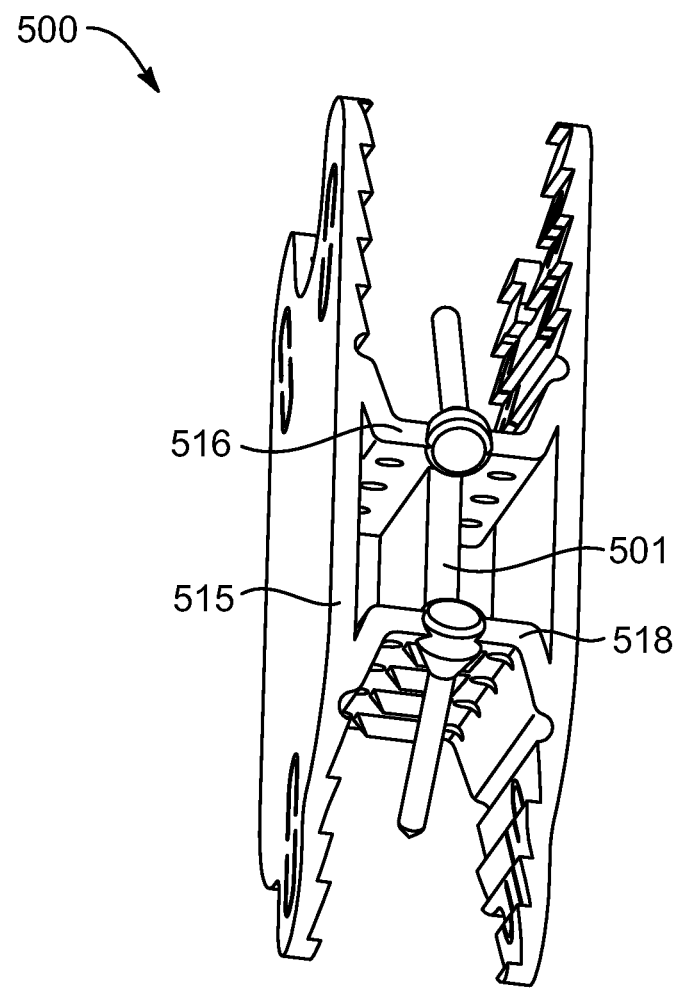
Figure 15:
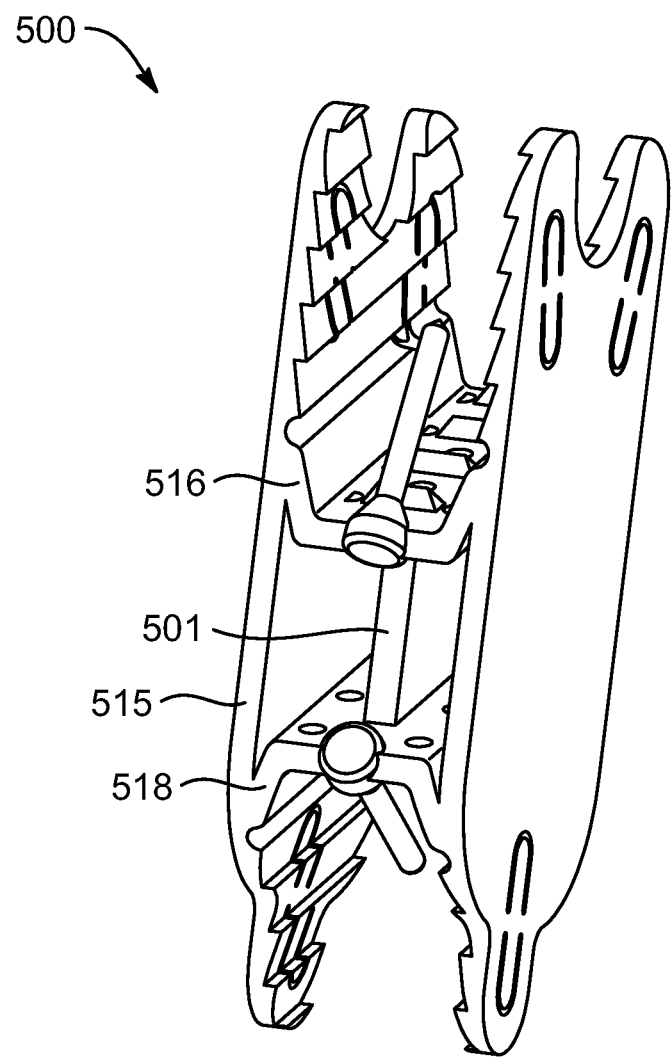
Figure 16:
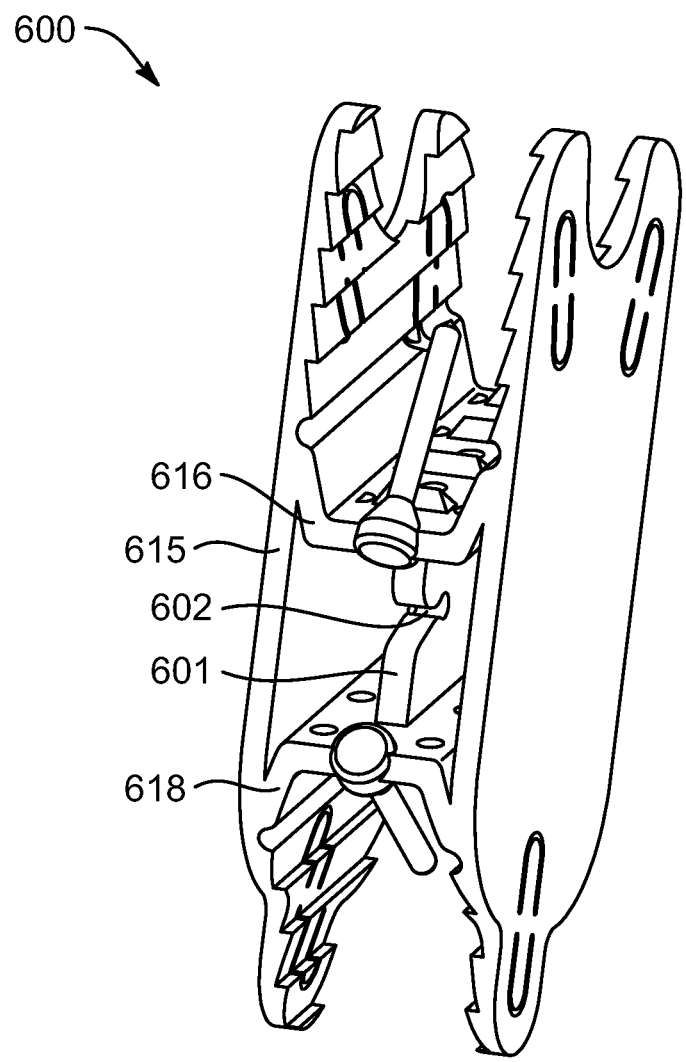
Figure 17:
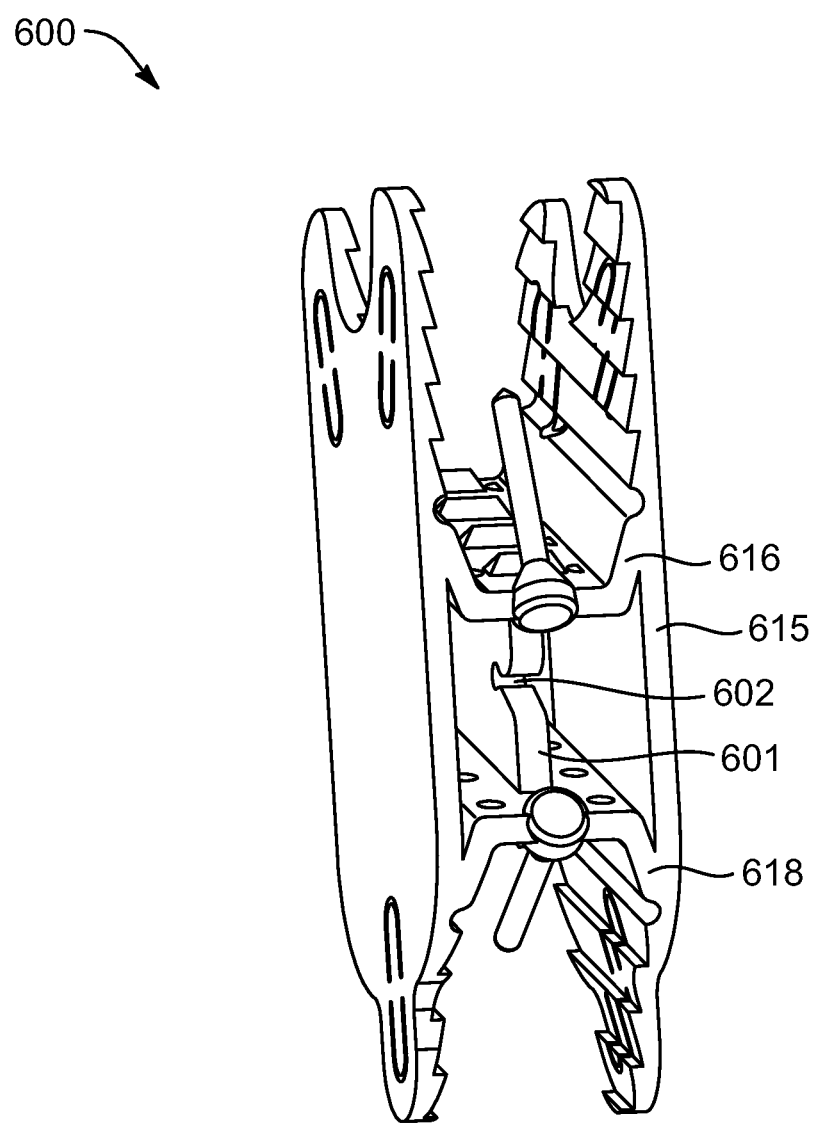
Figure 17:
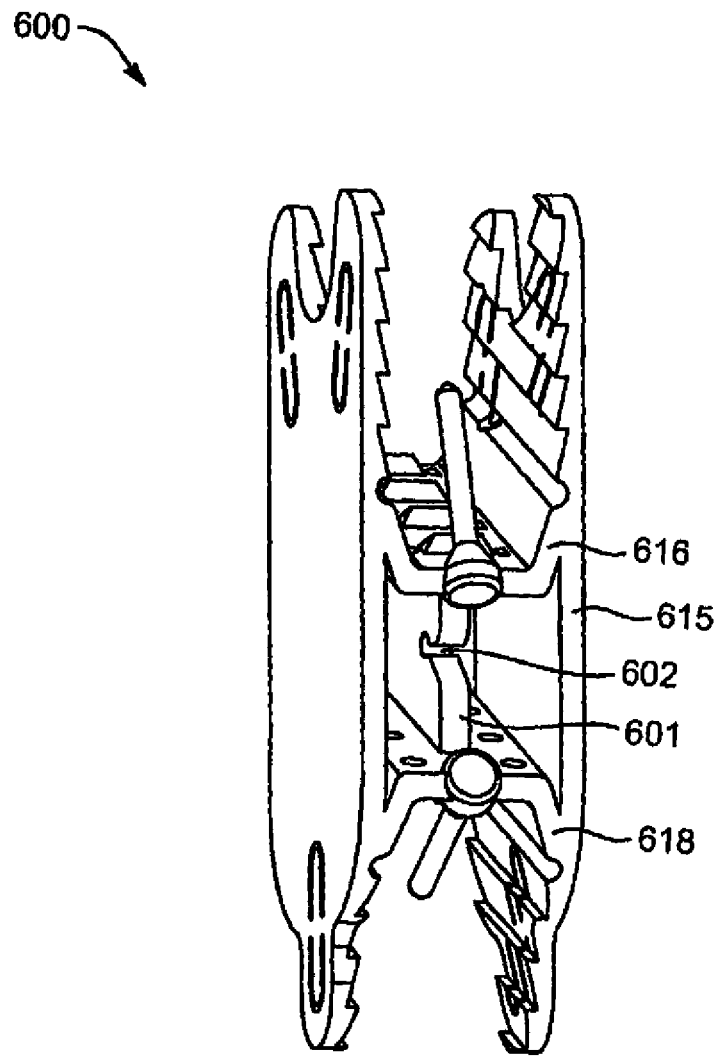

FIG. 1 is a first upper perspective view of a fusion member according to a first exemplary embodiment of the present disclosure;

FIG. 2 is an upper perspective view of the embodiment of FIG. 6;

FIG. 3 is a lower perspective view of the embodiment of FIG. 1;

FIG. 4 is an upper view of the embodiment of FIG. 1 in an installed position;

FIG. 5 is an upper perspective view of the embodiment of FIG. 1 in an installed position;

FIG. 6 is an upper perspective view of a fusion member according to a second exemplary embodiment of the present disclosure;

FIG. 7 is an upper perspective view of a fusion member according to a third exemplary embodiment of the present disclosure;

FIG. 8 is a lower perspective view of the embodiment of FIG. 7;

FIG. 9 is an upper perspective view of the embodiment of FIG. 7 in an installed position;

FIG. 10 is an side view of the embodiment of FIG. 7 in an installed position;

FIG. 11 is an upper perspective view of a fusion member according to a fourth exemplary embodiment of the present disclosure;

FIG. 12 is an upper view of the embodiment of FIG. 11 in an installed position;

FIG. 13 is an upper perspective view of a fusion member according to a fifth exemplary embodiment of the present disclosure;

FIG. 14 is an upper perspective view of a fusion member according to a sixth exemplary embodiment of the present disclosure;

FIG. 15 is a lower perspective view of the embodiment of FIG. 14;

FIG. 16 is an upper perspective view of a fusion member according to a seventh exemplary embodiment of the present disclosure; and FIG. 17 is a lower perspective view of the embodiment of FIG. 16.

DETAILED DESCRIPTION

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

Referring initially to FIGS. 1 and 3-5, an exemplary embodiment of a fusion member 100 comprises a cage 115 defining an inner volume 110 and paired extensions 120 and 130 extending from cage 115. FIGS. 4 and 5 illustrate fusion member 100 installed between a pair of spinous processes 210 and 220. As shown in FIG. 4, fusion member 100 generally forms an "H" shape in a posterior view, with extensions 120 forming ascending legs of the "H" shape and extensions 130 forming descending legs of the "H" shape. As used herein, the term "fusion member" is used to describe a member configured to promote fusion of vertebral processes.

In the embodiment shown, extensions 120 and 130 are configured so that they can be crimped (e.g, plastically deformed) onto spinous processes 210 and 220. Extensions 120 and 130 comprise gripping members 121 and 131, respectively, which assist in clamping fusion member 100 to spinous processes 210 and 220. The cage 115 may comprise gripping members 135 located between extensions 120 and 130.

Gripping members 121 and 131 allow fusion member 100 to be installed from a posterior direction so that extensions 120 and 130 can slide anteriorly along the sides of spinous processes 210 and 220. After fusion member 100 has been properly located between spinous processes 210 and 220, extensions 120 and 130 can be deformed so that gripping members 121 and 131 engage spinous processes 210 and 220. Specifically, extensions 120 can be crimped or deformed so that they are pinched toward each other so that gripping members 121 sink into spinous process 220. Similarly, extensions 130 can be crimped or deformed so that they are pinched toward each other to engage spinous process 210.

In this exemplary embodiment, gripping members 121, 131, and 135 are configured as sharp angled projections (e.g., teeth). In certain embodiments, gripping members 121, 131, and 135 may be configured as prongs, tines, tabs, barbs or spikes. In the embodiment shown, gripping members 121 and 131 are angled so that the projections point towards cage 115. Gripping members 121 and 131 are configured to allow translation between the fusion member 100 and a spinous process if the fusion member 100 is moved toward the engaged spinous process. This configuration restricts translation of the fusion member 100 in a direction away from the engaged spinous process. In the embodiment shown, gripping members 135 are pointed superiorly and inferiorly, and are configured to prevent translation in the posterior direction between the fusion member 100 and spinous processes 210 and 220.

Extensions 120 and 130 also comprise tabs 122 and 132, respectively, which assist in maintaining a fixed engagement between fusion member 100 and spinous processes 210 and 220. In certain embodiments, tabs 122 and 132 may be formed by removing material from extensions 120 and 130 in a pattern that forms tabs 122 and 132.

As shown in FIGS. 1 and 3-5, tabs 122 and 132 are in an undeformed condition wherein tabs 122 and 132 are parallel to extensions 120 and 130. After fusion member 100 is inserted between spinous processes 210 and 220, tabs 122 and 132 may be deformed (e.g., plastically deformed inward toward the space between extensions 120 and 130) so that tabs 122 and 132 further engage spinous processes 210 and 220. Tabs 122 and 132 may be deformed with a tool (e.g., forceps or a plier-type device, not shown) that comprise projections configured to engage tabs 122 and 132 and leverage members to provide easier deformation of the tabs. Tabs 122, 132 and gripping members 121, 131 serve to provide a positive engagement of fusion member 100 to spinous processes 210 and 220. In certain embodiments, fusion member 100 can provide fixation of spinous processes 210 and 220.

Cage 115 is shown in this embodiment to comprise a first end 116, a second end 118, a first side 117 and a second side 119. Cage 115 also comprise a lower surface 129, or lower cover, extending between first and second ends 116, 118 and first and second sides 117, 119. As explained in more detail below, lower surface 129 can assist in retaining bone fragments inserted into inner volume 110.

A plurality of bone fragments 145 (only a portion of which are shown in FIGS. 4 and 5) may be disposed within inner volume 110 to assist in fusing spinous processes 210 and 220 together. Cage 115 comprises a plurality of apertures 125 to promote fusion of the bone fragments 145 and spinous processes 210 and 220. In the exemplary embodiment shown, bone fragments 145 may be used to assist in inter-spinous process fusion. In other embodiments, bone fragments 145 may be used to assist in fusing various locations of adjacent vertebrae, including for example, inter-laminar fusion, facet fusion, inter-transverse process fusion, and inter-discal fusion. Bone fragments 145 may be of various sizes and shapes and may comprise bone autograft, allograft, or synthetic bone.

In the exemplary embodiment shown, extensions 120 comprise a recessed portion 123 in the area distal from cage 115. Extensions 130 comprise projections 133 in the area distal from cage 115. In certain embodiments, it may be desirable to utilize more than one fusion member 100. In such embodiments, the fusion members 100 can be arranged so that projections 133 fit into recessed portions 123. This can allow for closer spacing of fusion members 100.

Referring now to FIGS. 2 and 6, another embodiment of a fusion member 101 is equivalent to fusion member 100 shown and described above in FIGS. 1 and 3-5. Fusion member 101, however, does not comprise a lower surface 129. Still other exemplary embodiments may comprise a design similar to fusion member 100 with an additional upper surface, or upper cover, opposite of lower surface 129 to form a cage 115 that completely encloses the interior volume 110. The upper surface may be movable or installable to provide at least temporary access to the interior volume 110.

Referring now to FIGS. 7-10, an exemplary embodiment comprises a multi-piece fusion member 200. In this embodiment fusion member 200 comprises four separate components that can be assembled to form a unit that functions similar to previously-described fusion member 100. Fusion member 200 comprises a first clamping member 201, a second clamping member 202, a first plate 203, and a second plate 204. First plate 203 comprises a plurality of tabs 223 and second plate 204 comprises a plurality of tabs 233. When deformed, tabs 223 and 233 are configured to extend through slots 224 in first and second clamping members 201 and 202, respectively, and engage spinous processes 310 and 320 (shown in FIGS. 9 and 10). This configuration allows for first and second plates 203, 204 to remain coupled to first and second clamping members 201 and 202. First and second plates 203, 204 and first and second clamping members 201 and 202 may also comprise coupling or receiving members (not shown) including without limitation, threaded members, pins, eyelets, etc.

First clamping member 201 comprises a first end 216 and second clamping member comprises a second end 218. First end 216, second end 218, and the central portions of first plate 203 and second plate 204 combine to form a cage 215 defining an inner volume 210. Second plate 204 comprises a lower surface 229 (clearly visible in FIG. 8) configured to extend towards first plate 203. Lower surface 229 functions similar to previously described lower surface 129 of fusion member 100 and can serve to retain bone fragments 145 (not shown).

Referring now to FIGS. 11-12, another exemplary embodiment comprises a multi-piece fusion member 300 that is generally equivalent to the embodiment shown and described in FIGS. 7-10. This embodiment, however does not comprise a lower surface similar to lower surface 229 of the embodiment in FIGS. 7-10. As shown in FIG. 12, fusion member 300 is viewed from above in an installed position. Fusion member 300 is generally "H"-shaped when viewed from above.

Referring now to FIG. 13, another exemplary embodiment comprises a fusion member 400 similar to the one shown and described in FIGS. 1 and 3-5. This embodiment also comprises fastening members 490 configured to extend through first end 416 and second end 418 of cage 415. Fastening members 490 may comprise nails, screws, spikes, barbs, etc., and are configured to engage a spinous process inserted between extensions 420 and 430. Fastening members 490 can provide fixation of the fusion member 400 to the spinous processes in addition to that provided by gripping members 421 and 431 and tabs 422 and 432. Fastening member 490 may be preferentially positioned along a mid-sagittal plane bisecting the spinous process.

Referring now to FIGS. 14 and 15 another exemplary embodiment comprises a fusion member 500 similar to the one shown and described in FIG. 13. This embodiment comprises a septum or rib 501 extending between first end 516 and second end 518 of cage 515. Rib 501 can serve to provide structural rigidity to fusion member 500.

Referring now to FIGS. 16 and 17 another exemplary embodiment comprises a fusion member 600 similar to the one shown and described in FIGS. 14 and 15. This embodiment comprises a septum or rib 601 extending between first end 616 and second end 618 of cage 615. Rib 601 can serve to provide structural rigidity to fusion member 600. Rib 601 also comprises a receiving or securing feature 602. In the embodiment shown, securing feature 602 comprises a notch, but other exemplary embodiments may comprise different configurations, including for example, a pin, a hook, a spike, a barb, etc. Securing feature 602 can be configured to secure, for example, a shaped bone block (not shown) configured for insertion into cage 615.

Fusion members according to exemplary embodiments may be manufactured from suitable medical-grade materials, including, but not limited to, titanium and stainless steel.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. An H-shaped fusion system comprising:
  a cage forming a cross bar of the H-shape, wherein the cage comprises a first opening extending from a first open end of the cage to a second open end of the cage opposite the first open end;
  first and second plates projecting from the cage, the first and second plates forming a pair of ascending legs of the H-shape;
  third and fourth plates projecting from the cage, the third and fourth plates forming a pair of descending legs of the H-shape;
  a movable first cover over the first open end of the cage;

wherein, when a first spinous process is received between the first and second plates and a second spinous process is received between the third and fourth plates, the first opening extends in an anterior-posterior direction;
a first gripping member formed on the first plate, wherein the gripping member extends toward the second plate;
a second gripping member formed on the second plate, wherein the gripping member extends toward the first plate;
a third gripping member formed on the third plate, wherein the gripping member extends toward the fourth plate; and
a fourth gripping member formed on the fourth plate, wherein the gripping member extends toward the third plate.

2. The fusion system of claim 1, wherein the first cover is movable between a closed position in which the first cover blocks the first open end of the cage, and an open position in which the first cover is displaced so that the first open end of the cage is accessible.

3. The fusion system of claim 1, wherein the system comprises a graft securing feature inside the cage.

4. The fusion system of claim 3, wherein the graft securing feature is selected from the group consisting of a notch, a pin, a hook, a spike, and a barb.

5. The fusion member of claim 1, wherein the first, second, third, and fourth gripping members angle toward the cage.

6. An H-shaped fusion system comprising:
a cage forming a cross bar of the H-shape, wherein the cage comprises a first opening extending from a first open end of the cage to a second open end of the cage opposite the first open end;
first and second plates projecting from the cage, the first and second plates forming a pair of ascending legs of the H-shape;
third and fourth plates projecting from the cage, the third and fourth plates forming a pair of descending legs of the H-shape; and
a movable first cover over the first open end of the cage;
wherein, when a first spinous process is received between the first and second plates and a second spinous process is received between the third and fourth plates, the first opening extends in an anterior-posterior direction; and
wherein the fusion system further comprises at least one tab integrally formed within each of the first, second, third, and fourth plates, respectively, wherein each tab is deformable from an undeformed state, in which the tab is parallel with the corresponding plate, to a deformed state, in which the tab protrudes from the corresponding plate.

7. The fusion system of claim 6, wherein the tabs are integral with the first, second, third, and fourth plates, respectively, along a first side of each tab, wherein a slit separates all remaining sides of each tab from the corresponding plate.

8. The fusion system of claim 7, wherein the slit is U-shaped.

9. The fusion system of claim 6, comprising:
an undeformed state in which the first and second plates are spaced apart a first distance, the third and fourth plates are spaced apart a second distance, and the first tab is parallel to and flush with the at least one plate; and
a deformed state in which the first and second plates are spaced apart a third distance, the third and fourth plates are spaced apart a fourth distance, and the first tab protrudes from the at least one plate, wherein the third distance is less than the first distance and the fourth distance is less than the second distance;
wherein when the fusion member transforms from the undeformed state to the deformed state, the first, second, third, and fourth plates and the tab plastically deform.

10. The fusion member of claim 9, wherein, in the deformed state, the tab angles toward the cage.

11. The fusion member of claim 9, wherein, in the deformed state, the tab angles away from the cage.

12. The fusion member of claim 1, wherein the cage comprises a plurality of apertures.

13. The fusion member of claim 1, wherein each one of the first and second plates terminates with a recess opposite the cage, wherein each one of the third and fourth plates terminates with a projection opposite the cage, wherein the projection is complementary to the recess, with clearance.

14. The fusion member of claim 1, wherein the cage comprises a second opening extending beside the first opening, wherein the second opening extends from the first open end of the cage to the second open end of the cage, wherein the cage comprises a rib extending between the first and second openings and between the first and second open ends of the cage.

15. An H-shaped fusion member comprising:
a cage forming a cross bar of the H-shape;
first and second plates projecting from the cage, the first and second plates forming a pair of ascending legs of the H-shape;
third and fourth plates projecting from the cage, the third and fourth plates forming a pair of descending legs of the H-shape;
a graft securing feature inside the cage;
a first gripping member formed on the first plate, wherein the gripping member extends toward a second plate;
a second gripping member formed on the second plate, wherein the gripping member extends towards the first plate;
a third gripping member formed on the third plate, wherein the gripping member extends toward the fourth plate; and
a fourth gripping member formed on the fourth plate, wherein the gripping member extends towards the third plate;
wherein the cage comprises a first opening extending from a first open end of the cage to a second open end of the cage opposite the first open end, wherein, when a first spinous process is pinched between the first and second plates and a second spinous process is pinched between the third and fourth plates, the first opening extends in an anterior-posterior direction.

16. The fusion member of claim 15, wherein the graft securing feature is selected from the group consisting of a notch, a pin, a hook, a spike, and a barb.

17. The fusion member of claim 15, wherein the cage comprises a plurality of apertures.

18. The fusion member of claim 15, wherein the first, second, third, and fourth gripping members angle toward the cage.

19. An H-shaped fusion member comprising:
a cage forming a cross bar of the H-shape;
first and second plates projecting from the cage, the first and second plates forming a pair of ascending legs of the H-shape;
third and fourth plates projecting from the cage, the third and fourth plates forming a pair of descending legs of the H-shape; and
a graft securing feature inside the cage, and wherein the fusion member further comprises at least one tab integrally formed within each of the first, second, third, and fourth plates, respectively, wherein each tab is deformable from an undeformed state, in which the tab is parallel with the corresponding plate, to a deformed sate, in which the tab protrudes from the corresponding plate;

wherein the fusion member comprises an undeformed state in which the first and second plates are spaced apart a first distance, the third and fourth plates are spaced apart a second distance, and the first tab is parallel to and flush with the at least one plate;

wherein the fusion member comprises a deformed state in which the first and second plates are spaced apart a third distance, the third and fourth plates are spaced apart a fourth distance, and the first tab protrudes from the at least one plate, wherein the third distance is less than the first distance and the fourth distance is less than the second distance;

wherein, when the fusion member transforms from the undeformed state to the deformed state, the first, second, third, and fourth plates and the tab plastically deform; and wherein the cage comprises a second opening extending beside the first opening, wherein the second opening extends from the first open end of the cage to the second open end of the cage, wherein the cage comprises a rib extending between the first and second openings and between the first and second open ends of the cage.

20. The fusion member of claim 19, wherein the tabs are integral with the first, second, third, and fourth plates, respectively, along a first side of each tab, wherein a slit separates all remaining sides of each tab from the corresponding plate.

21. The fusion system of claim 20, wherein the slit is U-shaped.

22. The fusion member of claim 19, wherein, in the deformed state, the tab angles toward the cage.

23. The fusion member of claim 19, wherein, in the deformed state, the tab angles away from the cage.

24. An H-shaped fusion member comprising:
a cage forming a cross bar of the H-shape;
first and second plates projecting from the cage, the first and second plates forming a pair of ascending legs of the H-shape;
third and fourth plates projecting from the cage, the third and fourth plates forming a pair of descending legs of the H-shape;
a graft securing feature inside the cage;
a first gripping member formed on the first plate, wherein the gripping member extends toward a second plate;
a second gripping member formed on the second plate, wherein the gripping member extends towards the first plate;
a third gripping member formed on the third plate, wherein the gripping member extends toward the fourth plate; and
a fourth gripping member formed on the fourth plate, wherein the gripping member extends towards the third plate,
wherein the cage comprises a first opening extending from a first open end of the cage to a second open end of the cage opposite the first open end, wherein, when a first spinous process is pinched between the first and second plates and a second spinous process is pinched between the third and fourth plates, the first opening extends in an anterior-posterior direction, and wherein the fusion member further comprises a movable first cover over the first open end of the cage.

25. The fusion system of claim 24, wherein the first cover is movable between a closed position in which the first cover blocks the first open end of the cage, and an open position in which the first cover is displaced so that the first open end of the cage is accessible.

26. An H-shaped fusion member comprising:
a cage forming a cross bar of the H-shape;
first and second plates projecting from the cage, the first and second plates forming a pair of ascending legs of the H-shape;
third and fourth plates projecting from the cage, the third and fourth plates forming a pair of descending legs of the H-shape;
a graft securing feature inside the cage;
a first gripping member formed on the first plate, wherein the gripping member extends toward a second plate;
a second gripping member formed on the second plate, wherein the gripping member extends towards the first plate;
a third gripping member formed on the third plate, wherein the gripping member extends toward the fourth plate; and
a fourth gripping member formed on the fourth plate, wherein the gripping member extends towards the third plate;
wherein each one of the first and second plates terminates with a recess opposite the cage, wherein each one of the third and fourth plates terminates with a projection opposite the cage, wherein the projection is complementary to the recess, with clearance.

* * * * *

UNITED STATES PATENT AND TRADEMARK OFFICE
CERTIFICATE OF CORRECTION

| | |
|---|---|
| PATENT NO. | : 8,961,564 B2 |
| APPLICATION NO. | : 13/709251 |
| DATED | : February 24, 2015 |
| INVENTOR(S) | : Charles R. Gordon et al. |

It is certified that error appears in the above-identified patent and that said Letters Patent is hereby corrected as shown below:

In the Drawings:

Delete second occurrence of drawing sheet labeled "Sheet 16 of 17" and replace with missing drawing sheet labeled "Sheet 17 of 17" which is attached hereto.

Signed and Sealed this
Twenty-first Day of July, 2015

Michelle K. Lee
*Director of the United States Patent and Trademark Office*